United States Patent
Brendel et al.

(10) Patent No.: US 6,600,072 B2
(45) Date of Patent: Jul. 29, 2003

(54) SUBSTITUTED 1-NAPHTHOYLGUANIDINES, PROCESS FOR THEIR PREPARATION, THEIR USE AS A MEDICAMENT OR DIAGNOSTIC, AND MEDICAMENT CONTAINING THEM

(75) Inventors: Joachim Brendel, Bad Vilbel (DE); Heinz-Werner Kleeman, Bischofsheim (DE); Heinrich Christian Englert, Hofheim (DE); Hans Jochen Lang, Hofheim (DE); Udo Albus, Florstadt (DE); Bansi Lal, Bombay Pin (IN); Anil Vasantrao Ghate, Thane (IN)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/217,457

(22) Filed: Aug. 14, 2002

(65) Prior Publication Data

US 2003/0013760 A1 Jan. 16, 2003

Related U.S. Application Data

(63) Continuation of application No. 08/858,076, filed on May 16, 1997, now abandoned.

(30) Foreign Application Priority Data

May 29, 1996 (DE) .......................................... 196 21 482

(51) Int. Cl.[7] ..................... C07C 233/65; A61K 31/165
(52) U.S. Cl. ..................... 564/165; 564/164; 514/319; 514/620; 546/205
(58) Field of Search ................. 564/164, 165; 546/205; 514/319, 620

(56) References Cited

U.S. PATENT DOCUMENTS

| 4,251,545 A | 2/1981 | Resnick |
| 6,087,304 A | 7/2000 | Brendel |
| 6,093,729 A | 7/2000 | Schwark |

FOREIGN PATENT DOCUMENTS

| EP | 0 483 667 | 5/1992 |
| EP | 0 682 017 | 5/1995 |
| JP | 08-225 5135 | 9/1996 |
| WO | WO 94/26709 | 11/1994 |

*Primary Examiner*—Shailendra Kumar
(74) *Attorney, Agent, or Firm*—Finnegan, Henderson, Farabow, Garrett & Dunner, LLP

(57) ABSTRACT

Substituted 1-naphthoylguanidines, process for their preparation, their use as a medicament or diagnostic, and medicament containing them.

Substituted 1-naphthoylguanidines of the formula I

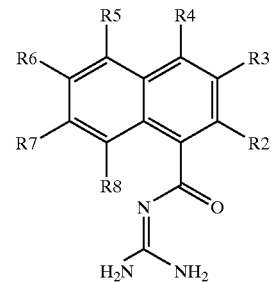

in which R2 to R8 have the meanings indicated in the claims, are suitable as antiarrhythmic pharmaceuticals having a cardioprotective component for infarct prophylaxis and infarct treatment and for the treatment of angina pectoris. They also preventively inhibit the pathophysiological processes in the formation of ischemically induced damage, in particular in the production of ischemically induced cardiac arrhythmias.

56 Claims, No Drawings

SUBSTITUTED 1-NAPHTHOYLGUANIDINES, PROCESS FOR THEIR PREPARATION, THEIR USE AS A MEDICAMENT OR DIAGNOSTIC, AND MEDICAMENT CONTAINING THEM

This is a continuation of application Ser. No. 08/858,076, filed May 16, 1997, now abandoned the contents of which is incorporated herein by reference.

The invention relates to substituted 1-naphthoylguanidines of the formula I

![Formula I structure showing naphthalene ring with substituents R2-R8 and an acylguanidine group]

in which:

R2, R3, R4, R5, R6, R7 and R8 independently of one another are H, F, Cl, Br, I, CN, $NO_2$, $CF_3$, $C_2F_5$ or $X_aY_bZ$;

X is O, S, NR(10), CR(11)R(12), C=O, C(=O)NR(10), C(=O)O, SO, $SO_2$, $SO_2$NR(10), OC=O, NR(10)C=O or NR(10)$SO_2$,
  where the linkage with the naphthalene ring in each case takes place via the left atom;
  R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is zero or 1;

Y is alkylene having 1, 2, 3, 4, 5, 6, 7 or 8 $CH_2$ groups, where one of these $CH_2$ groups can be replaced by O, S, NR(13) or o-, p- or m-phenylene;
  R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is H, alkyl having 1, 2, 3, 4, 5, 6 or 7 carbon atoms, cycloalkyl having 3, 4, 5, 6 or 7 carbon atoms, C(=O)R(15), $SO_2$R(15), NR(16)R(17) or phenyl, which is unsubstituted or substituted by 1–3 substituents selected from the group consisting of F, Cl, Br, $CF_3$, methyl, methoxy and NR(21)R(22);
  R(21) and R(22) independently of one another are H, alkyl having 1, 2, 3 or 4 carbon atoms or perfluoroalkyl having 1, 2, 3 or 4 carbon atoms;
  R(15) is N=C(NH$_2$)$_2$, NR(18)R(19), N(CH$_2$)$_c$NR(18)R(19) or OR(20);

c is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms;
or
R(18) and R(19) together are 4 or 5 methylene groups,
  of which one $CH_2$ group can be replaced by oxygen, S, NH, N—$CH_3$, N-benzyl or N-(p-chloro-phenyl);

R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one $CH_2$ group can be replaced by oxygen, S, NH, N—$CH_3$, N-benzyl or N-(p-chlorophenyl);
or
Z is an N-containing heterocycle having 1, 2, 3, 4, 5, 6, 7, 8 or 9 carbon atoms,
  where the N-containing heterocycle is linked via N or C and is unsubstituted or substituted by 1–3 substituents selected from the group consisting of F, Cl, Br, $CF_3$, methyl, methoxy and NR(21)R(22);

but where, in the case where R(4) is an alkoxy radical, at least one of the substituents R(2), R(3), R(5), R(6), R(7) and R(8) is not equal to hydrogen; and their pharmaceutically tolerable salts.

Preferred compounds of the formula I are those in which all substituents and indices are as defined above, but at least one of the substituents R2, R3, R4, R5, R6, R7 and R8 is not equal to hydrogen; and their pharmaceutically tolerable salts.

Compounds of the formula I are particularly preferred in which R2, R3, R5, R6, R7 and R8 are as defined at the beginning and R4 is H, F, Cl, Br, I, CN, $NO_2$, $CF_3$, $C_2F_5$ or Z where Z is defined as at the beginning, and their pharmaceutically tolerable salts.

Preferred compounds of the formula I are also those in which:

at least one of the substituents R2, R3, R4, R5, R6, R7 and R8 is $X_aY_bZ$;

X is O, S, NR(10), CR(11)R(12), C=O, C(=O)NR(10), C(=O)O, SO, $SO_2$, $SO_2$NR(10), OC=O, NR(10) C=O or NR(10)$SO_2$,
  where the linkage with the naphthalene ring in each case takes place via the left atom;
  R(10), R(11) and R(12) independently of one another are H, alkyl having 1, 2, 3 or 4 carbon atoms, perfluoroalkyl having 1 or 2 carbon atoms or cycloalkyl having 3, 4, 5 or 6 carbon atoms;

a is zero or 1;

Y is alkylene having 1, 2, 3, 4 or 5 $CH_2$ groups, where one of these $CH_2$ groups can be replaced by O, S, NR(13) or o-, p- or m-phenylene;
  R(13) is H, alkyl having 1, 2, 3 or 4 carbon atoms or cycloalkyl having 3, 4, 5, or 6 carbon atoms;

b is zero or 1;

Z is cycloalkyl having 3, 4, 5, 6 or 7 carbon atoms, C(=O)R(15), $SO_2$R(15), NR(16)R(17) or phenyl, which is unsubstituted or substituted by 1–3 substituents selected from the group consisting of F, Cl, Br, $CF_3$, methyl, methoxy and NR(21)R(22);
  R(21) and R(22) independently of one another are H, alkyl having 1, 2, 3 or 4 carbon atoms or perfluoroalkyl having 1 or 2 carbon atoms;
  R(15) N=C(NH$_2$)$_2$, NR(18)R(19), N(CH$_2$)$_c$NR(18(R(19) or OR(20);

R(18) and R(19) independently of one another are H, alkyl having 1, 2, 3, 4 or 5 carbon atoms;
or R(18) and R(19) together are 4 or 5 methylene groups,
of which one $CH_2$ group can be replaced by oxygen, S, NH, N—$CH_3$ or N-benzyl;
c is 2 or 3;
R(20) is H or alkyl having 1, 2, 3, 4, 5 or 6 carbon atoms;
R(16) and R(17) independently of one another are H, alkyl having 1, 2, 3, 4 or 5 carbon atoms or perfluoroalkyl having 1 or 2 carbon atoms;
or
R(16) and R(17) together are 4 or 5 methylene groups, of which one $CH_2$ group can be replaced by oxygen, S, NH, N—$CH_3$, N-benzyl or N-(p-chlorophenyl);
or
Z is an N-containing heterocycle having 1, 2, 3, 4, 5, 6, 7, 8 or 9 carbon atoms,
which is linked via N or C and is unsubstituted or substituted by 1–3 substituents selected from the group consisting of F, Cl, Br, $CF_3$, methyl, methoxy and NR(21)R(22);
and the other substituents R2, R3, R4, R5, R6, R7 and R8 in each case, which are still not allocated by the definition given above,
independently of one another are H, F, Cl, Br, I, CN, $NO_2$, $CF_3$, $C_2F_5$ or $X_aY_bZ$;
X is O, S, NR(10), C=O, C(=O)NR(10), C(=O)O, SO, $SO_2$, $SO_2$NR(10), OC=O, NR(10) C=O or NR(10)$SO_2$,
where the linkage with the naphthalene ring in each case takes place via the left atom;
R(10) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms,
a is zero or 1;
b is zero;
Z is H, alkyl having 1, 2, 3, 4 or 5 carbon atoms;
and their pharmaceutically tolerable salts.

Particularly preferred compounds of the formula I are those in which:
at least one of the substituents R2, R3, R4, R5, R6, R7 and R8 is $X_aY_bZ$;
X is O, NR(10), C(=O)NR(10), C(=O)O, $SO_2$NR(10), where the linkage with the naphthalene ring in each case takes place via the left atom;
R(10) is H or methyl;
a is 1;
Y is alkylene having 1, 2, 3, 4 or 5 $CH_2$ groups, where one of these $CH_2$ groups can be replaced by o-, p- or m-phenylene;
b is 1;
Z is C(=O)R(15), NR(16)R(17) or an N-containing heterocycle having 1, 2, 3, 4, 5, 6, 7, 8 or 9 carbon atoms,
where the N-containing heterocycle is linked via N or C and is unsubstituted;
R(15) is N=C($NH_2$)$_2$, NR(18)R(19), or OR(20);
R(18) and R(19) independently of one another are H, alkyl having 1, 2, 3 or 4 carbon atoms;
or
R(18) and R(19) together are 4 or 5 methylene groups,
of which one $CH_2$ group can be replaced by oxygen, S, NH, N—$CH_3$ or N-benzyl;
R(20) is H, alkyl having 1, 2 or 3 carbon atoms;
R(16) and R(17) independently of one another are H or alkyl having 1, 2, 3, 4 or 5 carbon atoms;
or
R(16) and R(17) together are 4 or 5 methylene groups, of which one $CH_2$ group can be replaced by oxygen, S, NH, N—$CH_3$, N-benzyl or N-(p-chlorophenyl);
and the other substituents R2, R3, R4, R5, R6, R7 and R8 in each case, which are still not allocated by the definition given above, independently of one another are H, F, Cl, Br, I, $CF_3$ or $X_aY_bZ$;
X is O, NR(10), C(=O)NR(10), C(=O)O, $SO_2$, $SO_2$NR(10), O C=O or NR(10) C=O,
where the linkage with the naphthalene ring in each case takes place via the left atom;
R(10) is H or alkyl having 1, 2 or 3 carbon atoms;
a is zero or 1;
b is zero;
Z is H or alkyl having 1, 2, 3 or 4 carbon atoms,
and their pharmaceutically tolerable salts.

If the compounds of the formula I contain one or more centers of asymmetry, these can have either the S or the R configuration. The compounds can be present as optical isomers, as diastereomers, as racemates or as mixtures thereof.

The alkyl radicals and perfluoroalkyl radicals designated can be either straight-chain or branched.

N-containing heterocycles having 1, 2, 3, 4, 5, 6, 7, 8 or 9 carbon atoms include, in particular, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, isoindolyl, benzimidazolyl, indazoyl, quinolyl, isoquinolyl, phthalazinyl, quinoxalinyl, quinazolinyl, cinnolinyl.

The N-containing heterocycles pyrrolyl, imidazolyl, quinolyl, pyrazolyl, pyridyl, pyrazinyl, pyrimidinyl and pyridazinyl are particularly preferred.

The invention furthermore relates to a process for the preparation of the compound 1, which comprises reacting a compound of the formula II

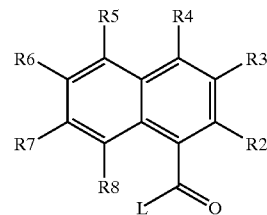

in which L is an easily nucleophilically substitutable leaving group and the other substituents have the abovementioned meaning, with guanidine.

The activated acid derivatives of the formula II in which L is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the underlying carbonyl chlorides (formula II, L=Cl), which for their part can in turn be prepared in a manner known per se from the underlying carboxylic acids (formula II, L=OH), for example using thionyl chloride.

In addition to the carbonyl chlorides of the formula II (L=Cl), other activated acid derivatives of the formula II can also be prepared in a manner known per se directly from the underlying naphthoic acid derivatives (formula II, L=OH), such as, for example, the methyl esters of the formula II where L=OCH₃ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II using Cl—COOC₂H₅ or tosyl chloride in the presence of triethylamine in an inert solvent; or the activation of the carboxylic acids can be carried out using dicyclohexylcarbodiimide (DCC) or using O-[(cyano(ethoxycarbonyl)methylene)amino]-1,1,3,3-tetramethyluronium tetrafluoborate ("TOTU") [Proceedings of the 21st European Peptide Symposium, Peptides 1990, Editors E. Giralt and D. Andreu, Escom, Leiden, 1991]. A number of suitable methods for the preparation of activated carboxylic acid derivatives of the formula II are given, with details of source literature, in J. March, Advanced Organic Chemistry, Third Edition (John Wiley & Sons, 1985), p. 350.

The reaction of an activated carboxylic acid derivative of the formula II with guanidine is carried out in a manner known per se in a protic or aprotic polar but inert organic solvent. Methanol, isopropanol or THF from 20° C. to the boiling point of these solvents have proven suitable in the reaction of the methyl naphthoates (II, L=OMe) with guanidine. In most reactions of compounds II with salt-free guanidine, the reaction was advantageously carried out in aprotic inert solvents such as THF, dimethoxyethane, dioxane or DMF. However, water can also be used as a solvent in the reaction of 11 with guanidine if a base such as, for example, NaOH is used.

If L=Cl, the reaction is advantageously carried out with the addition of an acid scavenger, for example in the form of excess guanidine for binding the hydrohalic acid.

Some of the underlying naphthoic acid derivatives of the formula II are known and described in the literature. The unknown compounds of the formula II can be prepared by methods known from the literature.

In general, carboxylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates, p-toluenesulfonates, maleates and fumarates.

The compounds I are substituted acylguanidines.

The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

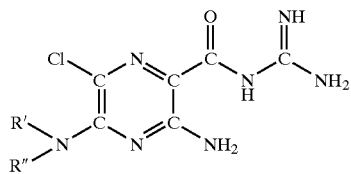

Amiloride: R', R"=H   Dimethylamiloride: R', R"=CH₃
Ethylisopropylamiloride: R'=C₂H₅, R"=CH(CH₃)₂

Investigations have moreover been disclosed which point to antiarrhythmic properties of amiloride (Circulation 79, 1257-63 (1989)). Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts [Eur. Heart J. 9 (suppl. 1): 167 (1988) (book of abstracts)]. For instance, it was found in rat hearts that an artificially induced ventricular fibrillation could be suppressed completely by amiloride. The above-mentioned amiloride derivative ethylisopropylamiloride was even more potent than amiloride in this model.

U.S. Pat. No. 4,251,545 discloses 1-naphthoylguanidines which are substituted in the 4-position by long-chain alkoxy groups. Use as fungicides in plant protection is described for these compounds.

The Patent Applications WO 94/26709 and EP-OS 682 017 disclose exclusively 2-naphthoylguanidines but no 1-naphthylguanidines. In these applications, the only example mentioned is unsubstituted 2-naphthoylguanidine.

The compounds known from the publications mentioned, however, do not fulfill all requirements which are necessary for the development of a medicament from a pharmacologically active compound. For example, better absorption, more favorable half-life times, better water solubility, lower toxicity or higher selectivity would be desirable.

This is achieved by the compounds according to the invention, which additionally exhibit no undesired and disadvantageous salidiuretic properties, but very good antiarrhythmic properties, such as are important, for example, for the treatment of diseases which are caused by oxygen deficiency. As a result of their pharmacological properties, the compounds, as antiarrhythmic pharmaceuticals having a cardioprotective component, are outstandingly suitable for infarct prophylaxis and infarct treatment and for the treatment of angina pectoris, where they also preventively inhibit or greatly reduce the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular Na⁺/H⁺ exchange mechanism as pharmaceuticals for the treatment of all acute or chronic damage caused by ischemia or primary or secondary diseases induced thereby. This relates to their use as pharmaceuticals for surgical interventions, for example in organ transplants, where the compounds can be used both for the protection of the organs in the donor before and during removal, for the protection of removed organs, for example during treatment or storage thereof in physiological bath fluids, and during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the CNS, where they are suitable, for example, for the treatment of stroke or of cerebral edema. Moreover the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action against the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophies and hyperplasias, in particular in prostate hyperplasia or prostate hypertrophy.

The compounds according to the invention are active inhibitors of the cellular sodium-proton antiporter ($Na^+/H^+$ exchanger), which is also raised in numerous diseases (essential hypertension, atherosclerosis, diabetes, etc.) in those cells which are easily accessible to measurements, such as, for example, in erythrocytes, platelets or leucocytes. The compounds according to the invention are therefore suitable as excellent and simple scientific tools, for example in their use as diagnostics for the determination and differentiation of certain forms of hypertension, but also of atherosclerosis, diabetes, proliferative diseases etc. Moreover, the compounds of the formula I are suitable for preventive therapy for the prevention of the formation of high blood pressure, for example, essential hypertension.

It has additionally been found that compounds of the formula I have a favorable effect on serum lipoproteins. It is generally recognized that for the formation of arteriosclerotic vascular changes, in particular of coronary heart disease, excessively high blood lipid values, so-called hyperlipoproteinaemias, are a significant risk factor. For the prophylaxis and the regression of atherosclerotic changes, the lowering of raised serum lipoproteins is therefore extremely important. Beside the reduction of the total serum cholesterol, the lowering of the proportion of specific atherogenic lipid fractions of this total cholesterol, in particular of the low density lipoproteins (LDL) and of the very low density lipoproteins (VLDL) is particularly important, as these lipid fractions are an atherogenic risk factor. In contrast, high density lipoproteins are ascribed a protective function against coronary heart disease. Accordingly, hypolipidaemics should be able not only to lower the total cholesterol, but in particular to lower the VLDL and LDL serum cholesterol fractions. It has now been found that compounds of the formula I have valuable therapeutically utilizable properties with respect to the effect on the serum lipid levels. Thus they significantly reduce the increased serum concentration of LDL and VLDL, as are to be observed, for example, due to increased dietetic intake of a cholesterol- and lipid-rich diet or in pathological metabolic disorders, for example genetically related hyperlipidaemias. They can therefore be used for the prophylaxis and for the regression of atherosclerotic changes in that they exclude a causal risk factor. These include not only the primary hyperlipidaemias, but also certain secondary hyperlipidaemias, such as occur, for example, in diabetes. Moreover, the compounds of the formula I lead to a distinct reduction of the infarct induced by metabolic anomalies and in particular to a significant reduction of the induced infarct size and its degree of severity. Compounds of the formula I furthermore lead to effective protection against endothelial damage induced by metabolic anomalies. With this protection of the vessels against the endothelial dysfunction syndrome, compounds of the formula I are valuable pharmaceuticals for the prevention and for the treatment of coronary vascular spasms, of atherogenesis and of atherosclerosis, of left-ventricular hypertrophy and of dilated cardiomyopathy, and of thrombotic disorders.

The compounds mentioned are therefore advantageously used for the production of a medicament for the treatment of hypercholesterolaemia; for the production of a medicament for the prevention of atherogenesis; for the production of a medicament for the prevention and treatment of atherosclerosis, for the production of a medicament for the prevention and treatment of illnesses which are caused by raised cholesterol levels, for the production of a medicament for the prevention and treatment of illnesses which are caused by endothelial dysfunction, for the production of a medicament for the prevention and treatment of atherosclerosis-induced hypertension, for the production of a medicament for the prevention and treatment of atherosclerosis-induced thromboses, for the production of a medicament for the prevention and treatment of hypercholesterolaemia- and endothelial dysfunction-induced ischaemic damage and postischaemic reperfusion damage, for the production of a medicament for the prevention and treatment of hypercholestrolaemia- and endothelial dysfunction-induced cardiac hypertrophies and cardiomyopathies, for the production of a medicament for the prevention and treatment of hypercholesterolaemia- and endothelial dysfunction-induced coronary vascular spasms and myocardial infarcts, for the production of a medicament for the treatment of the illnesses mentioned in combinations with hypertensive substances, preferably with angiotensin-converting enzyme (ACE) inhibitors and angiotensin receptor antagonists, a combination of an NHE inhibitor of the formula I with a hypolipidaemic active compound, preferably with an HMG-CoA reductase inhibitor (e.g. Lovastatin or Pravastatin), the latter contributing a hypolipidaemic action and thereby increasing the hypolipidaemic properties of the NHE inhibitor of the formula I and proving to be a favorable combination with increased action and reduced use of active compound.

The administration is therefore also claimed of sodium-proton exchange inhibitors of the formula I as pharmaceuticals for the lowering of increased blood lipid levels, and the combination of sodium-proton exchange inhibitors with pharmaceuticals having hypotensive and/or hypolipidaemic activity.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise both in veterinary and in human medicine.

The auxiliaries which are suitable for the desired pharmaceutical formulation are familiar to the person skilled in the art on the basis of his knowledge. In addition to solvents, gelling agents, suppository bases, tabletting auxiliaries and other active compound excipients, antioxidants, dispersants, emulsifiers, antifoams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular cornstarch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated. On average, the daily dose of a compound of the formula I in a patient of weight about 75 kg is at least 0.001 mg/kg, preferably 0.01 mg/kg, to at most 10 mg/kg, preferably 1 mg/kg of body weight. In acute episodes of the disease, for example immediately after suffering a cardiac infarct, even higher and in particular more frequent doses may be necessary, for example up to 4 individual doses per day. In particular when administered i.v., for example in the case of an infarct patient in the intensive care unit, up to 200 mg per day may be necessary.

Experimental Section

List of abbreviations:

| | |
|---|---|
| CDI | Carbonyldiimidazole |
| DMF | N,N-dimethylformamide |
| RT | Room temperature |
| M.p. | Melting point |
| FC | Flash chromatography |
| THF | Tetrahydrofuran |
| eq. | Equivalent |
| EA | Ethyl acetate (EtOAc) |

General Procedures for the Preparation of Naphthoylguanidines (I)

Variant 1 A: from naphthoic acids (II, L=OH)

1.0 eq. of the naphthoic acid derivative of the formula II is dissolved or suspended in anhydrous THF (5 ml/mmol) and then treated with 1.2 eq. of carbonyldiimidazole. After stirring for 2 hours at RT, 5.0 eq. of guanidine are introduced into the reaction solution. After stirring overnight, the THF is distilled off under reduced pressure (in a rotary evaporator), the residue is treated with water and the corresponding guanidine (formula I) is filtered off. The carboxylquanidines thus obtained can be converted into the corresponding salts by treating with aqueous, methanolic or ethereal hydrochloric acid or other pharmacologically tolerable acids.

Variant 1 B: from alkyl naphthoates (II, L=O-alkyl)

1.0 eq. of the alkyl carboxylates of the formula II and 5.0 eq. of guanidine (free base) are dissolved or suspended in isopropanol or in THF and boiled under reflux (typical reaction time 2 to 5 h) until conversion is complete (thin-layer checking). The solvent is distilled off under reduced pressure (rotary evaporator), and the residue is taken up in EA and washed 3 times with NaHCO$_3$ solution. It is dried over Na$_2$SO$_4$, the solvent is distilled off in vacuo and the residue is chromatographed on silica gel using a suitable eluent, e.g. EA/MeOH 5:1.

(For salt formation compare variant A)

General Procedure for the Alkylation of Hydroxynaphthoic Acid Esters 1.5 eq. of sodium methoxide are added to a solution of 1 eq. of a hydroxynaphthoic acid ester (e.g. methyl 6-hydroxynaphthoate or methyl 2-hydroxynaphthoate) in DMF (3 ml/mmol), and the mixture is stirred at 40° C. for 30 min. 1.7 eq of the alkylating agent (e.g. N-(2-chloroethylmorpholine)) are then added and the mixture is stirred, depending on the reactivity of the alkylating agent employed, at a temperature between 40° C. and 1 20° C. until reaction is complete (TLC checking, typical reaction time: 1–15 h).

EXAMPLE 1

4-Fluoro-1-naphthoylguanidine Hydrochloride

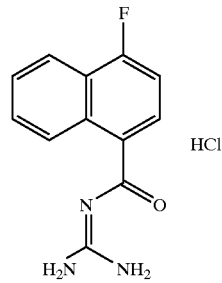

0.75 g of 4-fluoro-1-naphthoylguanidine hydrochloride was obtained from 1 g of 4-fluoro-1-naphthoic acid according to the general procedure 1A. M.p.: 245° C. 1H-NMR (DMSO-d6): δ [ppm]=7.5 (1H), 7.75 (2H), 8.1 (2H), 8.45 (1H), 8.7 (4H), 12.4 (1H).

EXAMPLE 2

5-Bromo-6-methoxy-1-naphthoylguanidine Hydrochloride

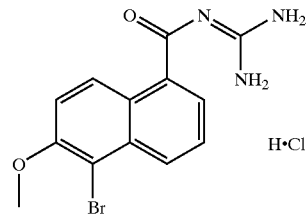

3.2 g of CDI are added to a suspension of 4.2 g of 5-bromo-6-methoxy-1-naphthoic acid (obtained from the methyl ester described in DE 4318069 by alkaline hydrolysis) in 90 ml of THF, and the mixture is stirred at RT overnight. It is treated with 4.4 g of guanidine and stirred at RT for 4 h, the THF is distilled off on a rotary evaporator and the residue is stirred with 100 ml of water. The precipitate which is deposited is filtered off with suction, dried and suspended in 60 ml of methanol. After addition of 3 ml of saturated isopropanolic hydrochloric acid and stirring for 30 minutes, the hydrochloride is filtered off with suction. 4.8 g of 5-bromo-6-methoxy-1-naphthoylguanidine hydrochloride are obtained; m.p.: >260° C. 1H-NMR (DMSO-d6): δ [ppm]=4.0 (3H), 7.6 (1H), 7.7 (1H), 7.9 (1H), 8.2–8.4 (6H), 12.1 (1H).

EXAMPLE 3

6-Methoxy-5-trifluoromethyl-1-naphthoyl-guanidine Hydrochloride

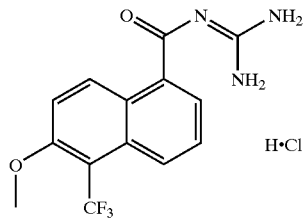

Analogously to Example 2, 4.7 g of 6-methoxy-5-trifluoromethyl-1-naphthoylguanidine hydrochloride were obtained from 4.0 g of 6-methoxy-5-trifluoromethyl-1-naphthoic acid (see EP 0059596, U.S. Pat. No. 4,590,010); m.p.: >260° C. 1H-NMR (DMSO-d6): δ [ppm]=4.0 (3H), 7.7 (2H), 7.9 (1H), 8.3 (1H), 8.5 (3H), 8.7 (2H), 12.3 (1H).

EXAMPLE 4

6-Methoxy-1-naphthoylguanidine Hydrochloride

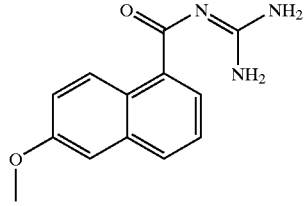

Analogously to Example 2, 1.2 g of 6-methoxy-1-naphthoylguanidine hydrochloride were obtained from 2.0 g of 6-methoxy-1-naphthoic acid; m.p.: 235–236° C. 1H-NMR (DMSO-d6): δ [ppm]=3.9 (3H), 7.3 (1H), 7.5 (1H), 7.6 (1H), 7.85 (1H), 8.1 (1H), 8.25 (1H), 8.6 (4H), 12.0 (1H).

EXAMPLE 5

6-(2-Diethylaminoethoxy)-1-naphthoylguanidine

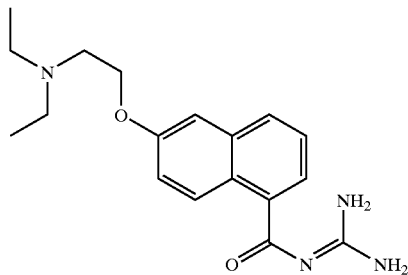

a) 200 g of 6-hydroxy-1-naphthoic acid are heated under reflux for 2 h in anhydrous methanol which has been saturated with HCl gas. The mixture is concentrated, the residue is recrystallized from methanol and 50 g of methyl 6-hydroxy-1-naphthoate are obtained.

b) 5 g of methyl 6-hydroxy-1-naphthoate and 2.0 g of sodium methoxide are stirred under $N_2$ at 40° C. for 20 min in 50 ml of DMF. 5.7 g of diethylaminoethyl chloride (free base) are then added and the mixture is stirred at 40° C. for a further 1 h. The DMF is stripped off on a rotary evaporator, the residue is taken up in dil. hydrochloric acid and the solution is extracted with ethyl acetate. The aqueous phase is rendered alkaline with sodium hydroxide solution and again extracted with ethyl acetate. After concentrating this extract, 6.2 g of methyl 6-(2-diethylaminoethoxy)-1-napthoate are obtained.

c) 6 g of methyl 6-(2-diethylaminoethoxy)-1-naphthoate and 6.8 g of KOH are dissolved in 150 ml of methanol and heated under reflux for 6 h. After adjusting the pH to 5.0, the methanol is distilled off in vacuo, and the residue is stirred with 500 ml of methylene chloride. After filtration and concentration of the filtrate, 2.2 g of 6-(2-diethylaminoethoxy)-1-naphthoic acid are obtained.

d) 1.5 g of CDI are added to a suspension of 2.0 g of 6-(2-diethylaminoethoxy)-1-naphthoic acid in 50 ml of THF, and the reaction mixture is stirred at RT overnight. It is then treated with 2.0 g of guanidine, again stirred overnight and concentrated, and the residue is stirred with 100 ml of water. The precipitate formed is filtered off with suction and purified by FC using methylene chloride/methanol 1:1. 0.66 g of 6-(2-diethylaminoethoxy)-1-naphthoylguanidine is obtained; m.p.: 168–169° C. $^1$H-NMR (DMSO-d6): δ [ppm]=1.0 (6H), 2.6 (4H), 2.85 (2H), 4.15 (2H), 7.15 (1H), 7.3 (1H), 7.4 (1H), 7.75 (2H), 8.7 (1H).

EXAMPLE 6

1-Naphthoylguanidine Hydrochloride; m.p. 160–162° C.

EXAMPLE 7

2-Hydroxy-1-naphthoylguanidine Hydrochloride Monohydrate; m.p.: 310° C.

EXAMPLE 8

2-Methoxy-1-naphthoylguanidine Hydrochloride; m.p. 263–264° C.

The following compounds were obtained analogously to the previously described methods by alkylation of methyl 1-hydroxynaphthoate and subsequent reaction with guanidine according to the general procedure, variant 1 b, or subsequent alkaline hydrolysis to give the corresponding naphthoic acid followed by guanidation according to variant 1 a:

EXAMPLE 9

2-(4-Bromobenzyloxy)naphthoylguanidine Hydrochloride Hemihydrate; m.p. 198–202° C.

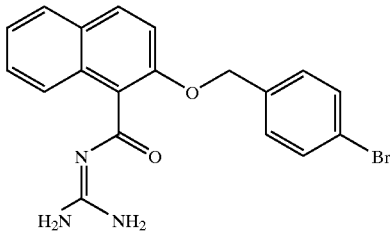

EXAMPLE 10

2-[4-(1-Piperidinomethyl)benzyloxy]-1-naphthoylguanidine; m.p. 205–210° C.

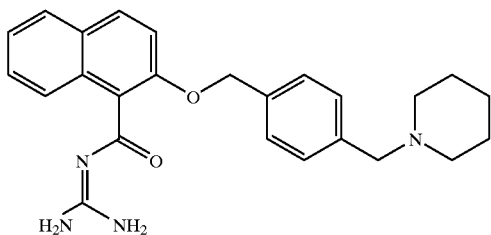

EXAMPLE 11

2-[4-(N,N-Dimethylaminomethyl)benzyloxy]-1-naphthoylguan idine Hydrochloride Monohydrate; m.p. 240° C.

EXAMPLE 12

2-[3-(N,N-Dimethylaminomethyl)benzyloxy]-1-naphthoylguanidine Hydrochloride Sesquihydrate; m.p. 209° C.

EXAMPLE 13

2-Propyloxy-1-naphthoylguanidine Hydrochloride; m.p. 235–237° C.

EXAMPLE 14

2-Butyloxy-1-naphthoylguanidine Hydrochloride; m.p. 215–216° C.

EXAMPLE 15

2-Isopentyloxy-1-naphthoylguanidine Hydrochloride; m.p. 235–237° C.

EXAMPLE 16

2-sec-Butyloxy-1-naphthoylguanidine Hydrochloride; m.p. 189–190° C.

EXAMPLE 17

2-Ethoxy-1-naphthoylguanidine Hydrochloride Hemihydrate; m.p. 247–248° C.

EXAMPLE 18

2-Isopropyloxy-1-naphthoylguanidine Hydrochloride; m.p. 219–223° C.

EXAMPLE 19

2-Benzyloxy-1-naphthoylguanidine Hydrochloride; m.p. 210–215° C.

EXAMPLE 20

2-Heptyloxy-1-naphthoylguanidine Hydrochloride; m.p. 180–185° C.

EXAMPLE 21

2-Cyclopentoxy-1-naphthoylguanidine Hydrochloride; m.p. 263–264° C.

EXAMPLE 22

4-Dimethylamino-1-naphthoylguanidine Hydrochloride

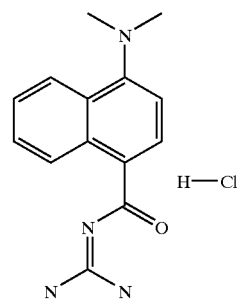

1.0 g of 4-dimethylamino-1-naphthoylguanidine hydrochloride is obtained from 1.0 g of 4-dimethylamino-1-naphthoic acid according to general procedure 1 A; $^1$H-NMR (DMSO-d6): δ [ppm]=3.0 (s, 6H), 7.2 (d, 1H), 7.6 (m, 2H), 8.1 (d, 1H), 8.3 (m, 1H), 8.5 (m, 1H), 8.7 (s,br., 4H), 12.1 (s, 1H).

EXAMPLE 23

Naphthaline-1,4-dicarboxylic Acid Diguanidide

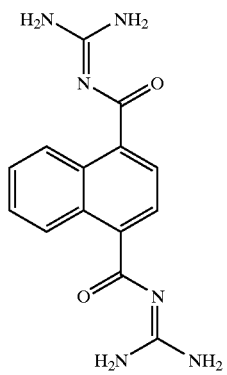

a) 5 g of naphthaline-1,4-dicarboxylic acid are dissolved in 50 ml of methanol, and the solution is treated with 10 ml of $SOCl_2$ and boiled under reflux for 6 h. The volatile constituents are removed in vacuo and the product is dried in vacuo. 5 g of dimethyl naphthaline-1,4-dicarboxylate are obtained as a colorless oil; MS (DCl):245 $(M+H)^+$.

b) 1.2 g of dimethyl naphthaline-1,4-dicarboxylate and 3 g of guanidine are dissolved in 10 ml of anhydrous isopropanol and the solution is boiled under reflux for 4 h. The solvent is removed in vacuo, the residue is slurried with water and the product is filtered off. 450 mg of naphthaline-1,4-dicarboxylic acid diguanidide are obtained; m.p.: 270° C. (Decomposition); $R_f$ (acetone/water 10:1)=0.14; MS (FAB):299 $(M+H)^+$.

Pharmacological Data:

Inhibition of the $Na^+/H^+$ exchanger of rabbit erythrocytes:

White New Zealand rabbits (Ivanovas) received a standard diet containing 2% cholesterol for six weeks in order to activate $Na^+/H^+$ exchange and thus to be able to determine the $Na^+$ influx into the erythrocytes via $Na^+/H^+$ exchange by flame photometry. The blood was taken from the auricular arteries and rendered uncoagulable by means of 25 lU/ml of potassium heparin. A part of each sample was used for the duplicate determination of the hematocrit by centrifugation. Aliquots of 100 μl in each case were used to measure the $Na^+$ starting content of the erythrocytes.

In order to determine the amiloride-sensitive sodium influx, 100 μl of each blood sample were incubated at pH 7.4 and 37° C. in 5 ml in each case of a hyperosmolar salt-sucrose medium (mmol/l: 140 NaCl, 3 KCl, 150 sucrose, 0.1 ouabain, 20 trishydroxymethylaminomethane). The erythrocytes were then washed three times with ice-cold $MgCl_2$-ouabain solution (mmol/l: 112 $MgCl_2$, 0.1 ouabain) and hemolyzed in 2.0 ml of distilled water. The intracellular sodium content was determined by flame photometry.

The net $Na^+$ influx was calculated from the difference between sodium starting values and the sodium content of the erythrocytes after incubation. The amiloride-inhibitable sodium influx ensued from the difference in the sodium content of the erythrocytes after incubation with and without amiloride $3 \times 10^{-4}$ mol/l. The sodium influx was also determined in this manner in the case of the compounds according to the invention.

Results for the inhibition of the $Na^+/H^+$ exchanger:

| Example | $IC_{50}$ [μmol/l] |
|---------|---------------------|
| 1       | 1–2                 |
| 5       | 1, 5                |
| 6       | 10                  |
| 8       | 0.5                 |
| 14      | 1                   |
| 18      | 2                   |
| 19      | 0, 3                |
| 22      | 0, 2                |

What is claimed is:
1. A substituted 1-naphthoylguanidine of the formula I

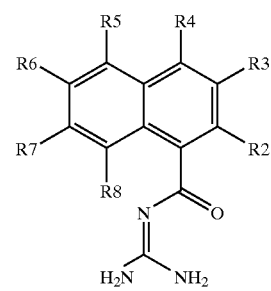

in which:
R2, R3, R4, R5, R6, R7 and R8 independently of one another are H, F, Cl, Br, I, CN, $NO_2$, $CF_3$, $C_2F_5$ or $X_aY_bZ$, but at least one of the substituents R2, R3, R4, R5, R6, R7 and R8 is not equal to hydrogen;

X is O, S, NR(10), CR(11)R(12), C=O, C(=O)NR(10), C(=O)O, SO, $SO_2$, $SO_2$NR(10), OC=O, NR(10) C=O or NR(10)$SO_2$,
where the linkage with the naphthalene ring in each case takes place via the left atom;

R(10), R(11) and R(12) independently of one another are H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;

a is 1;

Y is alkylene having 1, 2, 3, 4, 5, 6, 7 or 8 $CH_2$ groups, where one of these $CH_2$ groups can be replaced by O, S, NR(13) or o-, p- or m-phenylene;

R(13) is H, alkyl having 1, 2, 3, 4, 5 or 6 carbon atoms, perfluoroalkyl having 1, 2, 3 or 4 carbon atoms or cycloalkyl having 3, 4, 5 or 6 carbon atoms;

b is zero or 1;

Z is alkyl having 1, 2, 3, 4, 5, 6 or 7 carbon atoms, cycloalkyl having 3, 4, 5, 6 or 7 carbon atoms, C(=O)R(15), $SO_2$R(15), NR(16)R(17) or phenyl, which is unsubstituted or substituted by 1–3 substituents selected from the group consisting of F, Cl, Br, $CF_3$, methyl, methoxy and NR(21)R(22);

R(21) and R(22) independently of one another are H, alkyl having 1, 2, 3 or 4 carbon atoms or perfluoroalkyl having 1, 2, 3 or 4 carbon atoms;

R(1 5) is N=C(NH_2)_2, NR(18)R(19), N(CH_2)_cNR(18)R(19) or OR(20);

c is 2 or 3;

R(18) and R(19) independently of one another are H, alkyl having 1, 2, 3, 4, 5, 6, 7 or 8 carbon atoms or perfluoroalkyl having 1, 2, 3 or 4 carbon atoms;

or
R(18) and R(19) together are 4 or 5 methylene groups,
of which one $CH_2$ group can be replaced by oxygen, S, NH, N—$CH_3$, N-benzyl or N-(p-chlorophenyl);
R(20) is H, alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms;
R(16) and R(17) independently of one another are H, alkyl having 1, 2, 3, 4, 5, 6, 7 or 8 carbon atoms or perfluoroalkyl having 1, 2, 3 or 4 carbon atoms;
or
R(16) and R(17) together are 4 or 5 methylene groups, of which one $CH_2$ group can be replaced by oxygen, S, NH, N—$CH_3$, N-benzyl or N-(p-chlorophenyl);
or
Z is an N-containing heterocycle having 1, 2, 3, 4, 5, 6, 7, 8 or 9 carbon atoms,
where the N-containing heterocycle is linked via N or C and is unsubstituted or substituted by 1–3 substituents selected from the group consisting of F, Cl, Br, $CF_3$, methyl, methoxy and NR(21)R(22);
but where, in the case where R(4) is an alkoxy radical, at least one of the substituents R(2), R(3), R(5), R(6), R(7) and R(8) is not equal to hydrogen;
or its pharmaceutically tolerable salts.

2. A compound of the formula I as claimed in claim 1, in which:
R2, R3, R5, R6, R7 and R8 are as defined in claim 1;
R4 is H, F, Cl, Br, I CN, $NO_2$, $CF_3$, or $C_2F_5$.

3. A compound of the formula I as claimed in claim 1, in which:
at least one of the substituents R2, R3, R4, R5, R6, R7 and R8 is $X_aY_bZ$;
X is O, S, NR(10), CR(11)R(12), C=O, C(=O)NR(10), C(=O)O, SO, $SO_2$, $SO_2$NR(10), OC=O, NR(10) C=O or NR(10)$SO_2$,
where the linkage with the naphthalene ring in each case takes place via the left atom;
R(10), R(11) and R(12) independently of one another are H, alkyl having 1, 2, 3 or 4 carbon atoms, perfluoroalkyl having 1 or 2 carbon atoms or cycloalkyl having 3, 4, 5 or 6 carbon atoms;
a is zero or 1;
Y is alkylene having 1, 2, 3, 4 or 5 $CH_2$ groups,
where one of these $CH_2$ groups can be replaced by O, S, NR(13) or o-, p- or m-phenylene;
R(13) is H, alkyl having 1, 2, 3 or 4 carbon atoms or cycloalkyl having 3, 4, 5, or 6 carbon atoms;
b is zero or 1;
Z is cycloalkyl having 3, 4, 5, 6 or 7 carbon atoms, C(=O)R(15), $SO_2$R(15), NR(16)R(17) or phenyl, which is unsubstituted or substituted by 1–3 substituents selected from the group consisting of F, Cl, Br, $CF_3$, methyl, methoxy and NR(21)R(22);
R(21) and R(22) independently of one another are H, alkyl having 1, 2, 3 or 4 carbon atoms or perfluoroalkyl having 1 or 2 carbon atoms;
R(15) N=C(NH_2)_2, NR(18)R(19), N(CH_2)_cNR(18)R(19) or OR(20);
R(18) and R(19) independently of one another are H, alkyl having 1, 2, 3, 4 or 5 carbon atoms;
or
R(18) and R(19) together are 4 or 5 methylene groups,
of which one $CH_2$ group can be replaced by oxygen, S, NH, N—$CH_3$ or N-benzyl;
c is 2 or 3;
R(20) is H or alkyl having 1, 2, 3, 4, 5 or 6 carbon atoms;
R(16) and R(17) independently of one another are H, alkyl having 1, 2, 3, 4 or 5 carbon atoms or perfluoroalkyl having 1 or 2 carbon atoms;
or
R(16) and R(17) together are 4 or 5 methylene groups,
of which one $CH_2$ group can be replaced by oxygen, S, NH, N—$CH_3$, N-benzyl or N-(p-chlorophenyl);
or
Z is an N-containing heterocycle having 1, 2, 3, 4, 5, 6, 7, 8 or 9 carbon atoms,
which is linked via N or C and is unsubstituted or substituted by 1–3 substituents selected from the group consisting of F, Cl, Br, $CF_3$, methyl, methoxy and NR(21)R(22);
and the other substituents R2, R3, R4, R5, R6, R7 and R8 in each case, which are still not allocated by the definition given above, independently of one another are H, F, Cl, Br, 1, CN, $NO_2$, $CF_3$, $C_2F_5$ or $X_aY_bZ$;
X is O, S, NR(10), C=O, C(=O)NR(10), C(=O)O, SO, $SO_2$, $SO_2$NR(10), OC=O, NR(10) C=O or NR(10)$SO_2$,
where the linkage with the naphthalene ring in each case takes place via the left atom;
R(10) is H; alkyl having 1, 2, 3, 4, 5 or 6 carbon atoms, perfluoroalkyl having 1, 2, 3 or 4 carbon atoms or cycloalkyl having 3, 4, 5, 6 or 7 carbon atoms,
a is zero or 1;
b is zero;
Z is H, alkyl having 1,2, 3, 4 or 5 carbon atoms.

4. Compound of the formula I as claimed in claim 1 or 3, in which:
at least one of the substituents R2, R3, R4, R5, R6, R7 and R8 is $X_aY_bZ$;
X is O, NR(10), C(=O)NR(10), C(=O)O, $SO_2$NR(10), where the linkage with the naphthalene ring in each case takes place via the left atom;
R(10) is H or methyl;
a is 1;
Y is alkylene having 1, 2, 3, 4 or 5 $CH_2$ groups,
where one of these $CH_2$ groups can be replaced by o-, p- or m-phenylene;
b is 1;
Z is C(=O)R(15), NR(16)R(17) or an N-containing heterocycle having 1, 2, 3, 4, 5, 6, 7, 8 or 9 carbon atoms, where the N-containing heterocycle is linked via N or C and is unsubstituted;
R(15) is N=C(NH_2)_2, NR(18)R(19), or OR(20);
R(18) and R(19)
independently of one another are H, alkyl having 1, 2, 3 or 4 carbon atoms;
or
R(18) and R(19) together are 4 or 5 methylene groups, of which one $CH_2$ group can be replaced by oxygen, S, NH, N—$CH_3$ or N-benzyl;
R(20) is H, alkyl having 1, 2 or 3 carbon atoms;
R(16) and R(17) independently of one another are H or alkyl having 1, 2, 3, 4 or 5 carbon atoms;

or

R(16) and R(17) together are 4 or 5 methylene groups, of which one $CH_2$ group can be replaced by oxygen, S, NH, N—$CH_3$, N-benzyl or N-(p-chlorophenyl);

and the other substituents R2, R3, R4, R5, R6, R7 and R8 in each case, which are still not allocated by the definition given above, independently of one another are H, F, Cl, Br, I, $CF_3$ or $X_aY_bZ$;

X is O, NR(10), C(=O)NR(10), C(=O)O, $SO_2$, $SO_2$NR(10), OC=O or NR(10)C=O, where the linkage with the naphthalene ring in each case takes place via the left atom;

R(1 0) is H or alkyl having 1, 2 or 3 carbon atoms;

a is zero or 1;

b is zero;

Z is H or alkyl having 1, 2, 3 or 4 carbon atoms.

5. A compound of the formula I as claimed in claim 1 in which the compound is 4-Fluoro-1-naphthoylguanidine.

6. A compound of the formula I as claimed in claim 1 in which the compound is 4-Fluoro-1-naphthoylguanidine hydrochloride.

7. A compound of the formula I as claimed in claim 1 in which the compound is 5-Bromo-6-methoxy-1-naphthoylguanidine.

8. A compound of the formula I as claimed in claim 1 in which the compound is 5-Bromo-6-methoxy-1-naphthoylguanidine hydrochloride.

9. A compound of the formula I as claimed in claim 1 in which the 6-Methoxy-5-trifluoromethyl-1-naphthoyl-guanidine.

10. A compound of the formula I as claimed in claim 1 in which the compound is 6-Methoxy-5-trifluoromethyl-1-naphthoyl-guanidine hydrochloride.

11. A compound of the formula I as claimed in claim 1 in which the compound is 6-Methoxy-1-naphthoylguanidine.

12. A compound of the formula I as claimed in claim 1 in which the compound is 6-Methoxy-1-naphthoylguanidine hydrochloride.

13. A compound of the formula I as claimed in claim 1 in which the compound is 6-(2-Diethylaminoethoxy)-1-naphthoylguanidine.

14. A compound of the formula I as claimed in claim 1 in which the compound is 2-Hydroxy-1-naphthoylguanidine.

15. A compound of the formula I as claimed in claim 1 in which the compound is 2-Hydroxy-1-naphthoylguanidine hydrochloride monohydrate.

16. A compound of the formula,l as claimed in claim 1 in which the compound is 2-Methoxy-1-naphthoylguanidine.

17. A compound of the formula I as claimed in claim 1 in which the compound is 2-Methoxy-1-naphthoylguanidine hydrochloride.

18. A compound of the formula I as claimed in claim 1 in which the compound is 2-(4-Bromobenzyloxy) naphthoylguanidine.

19. A compound of the formula I as claimed in claim 1 in which the compound is 2-(4-Bromobenzyloxy) naphthoylguanidine hydrochloride hemihydrate.

20. A compound of the formula I as claimed in claim 1 in which the compound is 2-[4-(1-Piperidinomethyl) benzyloxy]-1-naphthoylguanidine.

21. A compound of the formula I as claimed in claim 1 in which the compound is 2-[4-(N,N-Dimethylaminomethyl) benzyloxy]-1-naphthoylguanidine.

22. A compound of the formula I as claimed in claim 1 in which the compound is 2-[4-(N,N-Dimethylaminomethyl) benzyloxy]-1-naphthoylguanidine hydrochloride monohydrate.

23. A compound of the formula I as claimed in claim 1 in which the compound is 2-[3-(N,N-Dimethylaminormethyl) benzyloxy]-1-naphthoylguanidine.

24. A compound of the formula I as claimed in claim 1 in which the compound is 2-[3-(N,N-Dimethylaminomethyl) benzyloxy]-1-naphthoylguanidine hydrochloride sesquihydrate.

25. A compound of the formula I as claimed in claim 1 in which the compound is 2-Propyloxy-1-naphthoylguanidine.

26. A compound of the formula I as claimed in claim 1 in which the compound is 2-Propyloxy-1-naphthoylguanidine hydrochloride.

27. A compound of the formula I as claimed in claim 1 in which the compound is 2-Butyloxy-1-naphthoylguanidine.

28. A compound of the formula I as claimed in claim 1 in which the compound is 2-Butyloxy-1-naphthoylguanidine hydrochloride.

29. A compound of the formula I as claimed in claim 1 in which the compound is 2-lsopentyloxy-1-naphthoylguanidine.

30. A compound of the formula I as claimed in claim 1 in which the compound is 2-lsopentyloxy-1-naphthoylguanidine hydrochloride.

31. A compound of the formula I as claimed in claim 1 in which the compound is 2-sec-Butyloxy-1-naphthoylguanidine.

32. A compound of the formula I as claimed in claim 1 in which the compound is 2-sec-Butyloxy-1-naphthoylguanidine hydrochloride.

33. A compound of the formula I as claimed in claim 1 in which the compound is 2-Ethoxy-1-naphthoylguanidine.

34. A compound of the formula I as claimed in claim 1 in which the compound is 2-Ethoxy-1-naphthoylguanidine hydrochloride hemihydrate.

35. A compound of the formula I as claimed in claim 1 in which the compound is 2-Isopropyloxy-1-naphthoylguanidine.

36. A compound of the formula I as claimed in claim 1 in which the compound is 2-Isopropyloxy-1-naphthoylguanidine hydrochloride.

37. A compound of the formula I as claimed in claim 1 in which the compound is 2-Benzyloxy-1-naphthoylguanidine.

38. A compound of the formula I as claimed in claim 1 in which the compound is 2-Benzyloxy-1-naphthoylguanidine hydrochloride.

39. A compound of the formula I as claimed in claim 1 in which the compound is 2-Heptyloxy-1-naphthoylguanidine.

40. A compound of the formula I as claimed in claim 1 in which the compound is 2-Heptyloxy-1-naphthoylguanidine hydrochloride.

41. A compound of the formula I as claimed in claim 1 in which the compound is 2-Cyclopentoxy-1-naphthoylguanidine.

42. A compound of the formula I as claimed in claim 1 in which the compound is 2-Cyclopentoxy-1-naphthoylguanidine hydrochloride.

43. A compound of the formula I as claimed in claim 1 in which the compound is 4-Dimethylamino-1-naphthoylguanidine.

44. A compound of the formula I as claimed in claim 1 in which the compound is 4-Dimethylamino-1-naphthoylguanidine hydrochloride.

45. A compound of the formula I as claimed in claim 1 in which the compound is Naphthaline-1,4-dicarboxylic acid diguanidide.

46. A pharmaceutical composition comprising an effective amount of a compound of the formula I as claimed in claim 1.

47. A method of treating or prophylaxis of illnesses caused by ischaemic conditions comprising administering an effective amount of a compound I as claimed in claim 1.

48. A method of treating arrhythmias comprising administering an effective amount of a compound I as claimed in claim 1.

49. A method of treating or prophylaxis of cardiac infarct comprising administering an effective amount of a compound I as claimed in claim 1.

50. A method of treating or prophylaxis of angina pectoris comprising administering an effective amount of a compound I as claimed in claim 1.

51. A method of treating or prophylaxis of ischemic conditions of the heart comprising administering an effective amount of a compound I as claimed in claim 1.

52. A method of treating or prophylaxis of ischemic conditions of the peripheral comprising administering an effective amount of a compound I as claimed in claim 1.

53. A method of treating or prophylaxis of ischemic conditions of the central nervous system comprising administering an effective amount of a compound I as claimed in claim 1.

54. A method of treating or prophylaxis of stroke comprising administering an effective amount of a compound I as claimed in claim 1.

55. A method of treating of states of shock comprising administering an effective amount of a compound I as claimed in claim 1.

56. A method of treating illnesses in which cell proliferation is a primary or secondary cause, primary or secondary cause, and thus the use as antiathero-sclerotic, agents against diabetic related complications, carcinosis, fibrotic disorders such as pulmonary fibrosis, fibrosis of the liver or fibrosis of the kidney, and prostate hyperplasia comprising administering an effective amount of a compound I as claimed in claim 1.

* * * * *

UNITED STATES PATENT AND TRADEMARK OFFICE
CERTIFICATE OF CORRECTION

PATENT NO. : 6,600,072 B2
DATED : July 29, 2003
INVENTOR(S) : Brendel et al.

It is certified that error appears in the above-identified patent and that said Letters Patent is hereby corrected as shown below:

Column 16,
Line 36, "NR(10) C=O" should read -- NR(10)C=O --.
Line 62, "R(1 5)" should read -- R(15) --.

Column 17,
Line 41, "NR(10) C=O" should read -- NR(10)C=O --.

Column 18,
Line 27, "1," should read -- I, --.
Line 29, "NR(10) C=O" should read -- NR(10)C=O --.
Line 33, "H;" should read -- H, --.
Line 39, "1,2," should read -- 1, 2, --.

Column 19,
Line 9, "O." should read -- O, --.
Line 13, "R(1 0)" should read -- R(10) --.
Line 29, after "which the" insert -- compound is --.
Line 47, "formula,1" should read -- formula I --.

Column 20,
Lines 2-3, "2-[3-(N,N-Dimethylaminormethyl)benzyloxy]-1-naphthoylguanidine." should read -- 2-[3-(N,N-Dimethylaminomethyl)benzyloxy]-1-naphthoylguanidine. --.
Lines 20-21, "2-lsopentyloxy-1-naphthoylguanidine." should read -- 2-Isopentyloxy-1-naphthoylguanidine. --.
Lines 23-24, "2-lsopentyloxy-1-naphthoylguanidine" should read -- 2-Isopentyloxy-1-naphthoylguanidine --.

UNITED STATES PATENT AND TRADEMARK OFFICE
CERTIFICATE OF CORRECTION

PATENT NO. : 6,600,072 B2
DATED : July 29, 2003
INVENTOR(S) : Brendel et al.

It is certified that error appears in the above-identified patent and that said Letters Patent is hereby corrected as shown below:

<u>Column 22,</u>
Line 14, "antiathero-sclerotic," should read -- antiatherosclerotic, --.

Signed and Sealed this

Twenty-eighth Day of October, 2003

JAMES E. ROGAN
*Director of the United States Patent and Trademark Office*